United States Patent [19]

Shaw

[11] Patent Number: 4,739,121
[45] Date of Patent: Apr. 19, 1988

[54] PROCESS FOR OTHO- AND PARA-ALKYLATING DIPHENYLAMINES

[75] Inventor: Chong-Kuang Shaw, Broadview Heights, Ohio

[73] Assignee: The B. F. Goodrich Company, Akron, Ohio

[21] Appl. No.: 904,078

[22] Filed: Sep. 4, 1986

Related U.S. Application Data

[63] Continuation-in-part of Ser. No. 613,671, May 24, 1984, abandoned.

[51] Int. Cl.⁴ ............................................. C07C 85/24
[52] U.S. Cl. .................................................. 564/409
[58] Field of Search ............... 564/409, 437, 433, 209; 502/26, 35, 27

[56] References Cited

U.S. PATENT DOCUMENTS

| | | | |
|---|---|---|---|
| 2,530,769 | 11/1950 | Hollis | 252/401 |
| 2,762,845 | 9/1956 | Stroh et al. | 260/578 |
| 2,814,646 | 11/1957 | Kolka et al. | 260/577 |
| 2,943,112 | 6/1960 | Popoff et al. | 260/576 |
| 3,505,225 | 4/1970 | Wheeler | 252/33.6 |
| 3,655,559 | 4/1972 | Holt | 252/51.5 A |
| 3,732,167 | 5/1973 | Foucher et al. | 252/32.7 E |
| 3,909,425 | 9/1975 | Wheeler | 252/32.7 E |
| 3,923,892 | 12/1975 | Osakar | 260/578 |
| 4,069,268 | 1/1978 | Siskin et al. | 260/666 P |

OTHER PUBLICATIONS

J. Org. Chem. 21, 711–713, (1956).
Angew. Chem. 69, 124–131, (1957).

*Primary Examiner*—J. E. Evans
*Attorney, Agent, or Firm*—Alan A. Csontos; George A. Kap

[57] ABSTRACT

Ortho-para-alkylated diphenylamines are prepared utilizing an improved, one-stage process wherein the diphenylamines are ortho-alkylated by reaction with a first olefin in the presence of an aluminum complex as the catalyst, and are subsequently para-alkylated by reaction with a second olefin using a Friedel-Crafts aluminum catalyst. The para-alkylation is carried out without prior isolation or solvent washing of the ortho-alkylated diphenylamine intermediates.

8 Claims, No Drawings

PROCESS FOR OTHO- AND PARA-ALKYLATING DIPHENYLAMINES

CROSS-REFERENCE TO A RELATED APPLICATION

This application is a continuation-in-part of prior application Ser. No. 613,671 filed on May 24, 1984, now abandoned.

BACKGROUND OF THE INVENTION

Alkylated derivatives of diphenylamines are well known compounds that are commonly used as antioxidants for lubricating oils, natural and synthetic rubbers and plastics. Alkylated diphenylamine compounds include, for example; 4,4'-bis($\alpha,\alpha$-dimethylbenzyl)diphenylamine as described in U.S. Pat. No. 3,505,225; 2,2'-diethyl-4,4'-tert-dioctyldiphenylamine as described in U.S. Pat. No. 3,732,167; 2,2',4,4'-tetra-t-butyldiphenylamine as described in U.S. Pat. No. 3,655,559; and p,p'-di-tertiary-octyl-diphenylamine and p,p'-di-($\alpha$-phenylethyl)diphenylamine as described in U.S. Pat. No. 2,530,769. Alkylated diphenylamines are typically prepared by alkylating a diphenylamine with olefins such as ethylene, heptene, octene, nonene, styrene, and diisobutylene, in the presence of a suitable alkylation catalyst. For example, U.S. Pat. No. 2,530,769 discloses the para-alkylation of diphenylamines using various olefins and a Friedel-Crafts condensation catalyst such as aluminum chloride, and U.S. Pat. No. 2,943,112 discloses the alkylation of diphenylamine with heptenes, octenes, and nonenes using a Filtrol Clay as a catalyst.

As to the ortho-alkylation step, an article in the "Journal of Organic Chemistry", Vol. 21, page 711 (1956) discloses a process and mechanism for ortho-alkylating aromatic amines using aluminum metal to form an aluminum anilide catalyst. U.S. Pat. Nos. 2,762,845 and 2,814,646 also discloses the use of aluminum metal to form an aluminum anilide to effect the ortho-alkylation of aromatic amines. The U.S. Pat. No. 2,814,646 also discloses that aluminum halide used with an alkali or alkaline earth metal anilide can be used in the ortho-reaction. U.S. Pat. No. 3,923,892 discloses the use of an alkylaluminum halide with aromatic amines to achieve accelerated reaction rates. An article in the German journal Angewandte Chemie, Volume 69, page 124 (1957) discloses the ortho-alkylation of diphenylamine using as a catalyst the reaction product of aluminum metal with aniline.

Ortho-para-alkylated diphenylamines are typically synthesized in a two-stage process. In the first stage, diphenylamine is alkylated at one or both of the ortho-(2 and 2') positions by reacting with a suitable olefin and typically using an aluminum catalyst. The ortho-alkylated product is then isolated, generally by fractional distillation or by washing the crude mixture with water, and subsequently para-alkylated at one or both of the para-(4 and 4') positions with additional olefin. The U.S. Pat. No. 3,655,559 referenced above describes such a general process, wherein the ortho-alkylation is first performed by reacting diphenylamine with a 2 to 4 carbon olefin, and the para-alkylation involves the subsequent reaction of the ortho-alkylated diphenylamine with a secondary olefin having 4 to 12 carbons, such as isobutylene, 2-methyl pentene-1, diisobutylene and propylene trimer. Although the U.S. Pat. No. 3,655,559 discloses a preparation of a tetra-substituted product in a single-stage alkylation where the ortho- and para-substituents are the same t-butyl groups, for different alkyl substituents at the ortho- and para-positions the two-stage alkylation is disclosed.

The necessity for isolation of the ortho-alkylated diphenylamine intermediate prior to the para-alkylation introduces an undesirable step with attendant disadvantages. The isolation step results in additional process equipment requirements, longer preparation times, lower productivity, increased catalyst usage, and increased costs. An alkylation process which can effectively produce ortho-para-alkylated diphenylamines having different ortho- and para-substituents, without the necessity for isolation of the ortho-alkylated intermediate, is most desirable.

It is an object of the present invention to provide an improved process for ortho-para-alkylation of diphenylamines wherein the intermediate product does not have to be isolated. It is a further object of this invention to achieve a more efficient process for the preparation of ortho-para-alkylated diphenylamines where the ortho- and para-substituents are different entities.

SUMMARY OF THE INVENTION

This invention is an improved, one-stage process for alkylation of diphenylamines which comprises (1) forming a reactive aluminum complex by the interaction of diphenylamines and aluminum, (2) ortho-alkylating the diphenylamines by reaction with a first olefin in the presence of the aluminum complex, (3) adding hydrogen halide to the ortho-alkylated diphenylamine intermediate products to form a Friedel-Crafts aluminum catalyst, and (4) subsequently para-alkylating the ortho-alkylated intermediates by reaction with a second olefin in the presence of the Friedel-Crafts aluminum catalyst, without prior isolation or solvent washing of the ortho-alkylated intermediates. Although the present inventive process is readily usable to produce alkylated diphenylamines where all the ortho- and para-substituents are the same, the process is particularly applicable to the production of alkylated diphenylamines with different ortho- and para-substituents, such as, for example, the preparation of 4,4'-bis($\alpha,\alpha$-dimethylbenzyl)2,2'-diethyl-diphenylamine.

DETAILED DESCRIPTION

This invention relates to an improved process for ortho-, para-alkylation of diphenylamines. Specifically, this invention involves an improved, one-stage process for ortho- para-alkylation of diphenylamines which comprises (1) forming a reactive aluminum complex by the interaction of diphenylamines and aluminum, (2) ortho-alkylating the diphenylamines with a first olefin in the presence of the aluminum complex, (3) adding hydrogen halide to the ortho-alkylated diphenylamine intermediate products to form a Friedel-Crafts aluminum catalyst, and (4) subsequently para-alkylating the ortho-alkylated diphenylamine intermediates by reacting the intermediate with a second olefin in the presence of the Friedel-Crafts aluminum catalyst, wherein the para-alkylation is carried out without prior isolation or solvent washing of the ortho-alkylated intermediates.

The present process is suitable for the synthesis of alkylated diphenylamines represented by the general formula:

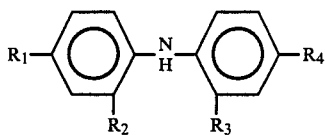

wherein $R_1$ and $R_4$ represent the same of different linear or branched alkyl radicals having 2 to about 12 carbon atoms or alkaryl radicals having from 8 to about 16 carbon atoms, and $R_2$ and $R_3$ represent the same or different linear alkyl radicals having from 2 to about 10 carbon atoms or branched alkyl radicals having from 3 to about 6 carbon atoms. More preferably, $R_1$ and $R_4$ are the same radicals and are linear or branched alkyl radicals of about 4 to about 9 carbon atoms such as t-butyl, t-octyl or nonyl groups, or alkaryl radicals of 8 to about 12 carbon atoms such as α-methyl benzyl groups. Also, more preferredly, $R_2$ and $R_3$ are the same radicals and are ethyl groups or branched alkyl radicals of 3 to 6 carbon atoms such as isopropyl or t-butyl groups. Alkylated diphenylamines which can be made by the present invention include, for example: 2,2'-diethyl,4,4'-t-dioctyldiphenylamine; 2,2'-diethyl-4,4'-di-t-butyldiphenylamine; 2,2'-diethyl-4,4'-bis(α,α-dimethylbenzyl)-diphenylamine, 2,2'-diethyl-4,4'-dinonyldiphenylamine, and the like. The process is particularly suitable for the preparation of ortho-para-diphenylamines having different ortho- and para-substituents.

The ortho-alkylation is carried out in a closed reaction vessel by reacting the diphenylamine with a first olefin containing 2 to 10 carbon atoms. The ortho-alkylation is conducted at a temperature from about 180° C. to about 260° C., at a pressure from about 50 to about 300 psig, for about 30 minutes to about 6 hours or more in the presence of an aluminum complex as the catalyst. The aluminum complex is formed by the interaction of aluminum metal with the diphenylamine. The aluminum is employed either as aluminum metal in combination with aluminum chloride which is believed to act as a catalyst, or as a combination of aluminum chloride with an alkali metal. The combination of aluminum chloride plus an alkali metal such as sodium, forms the aluminum complex faster. The total amount of aluminum in the form of aluminum and/or aluminum chloride is employed in an effective amount, typically ranging from about 0.1 to about 10 mole percent of aluminum per mole of diphenylamine, and more preferably ranges from about 1 to about 8 mole percent of aluminum per mole of diphenylamine. When the ortho-alkylation catalyst is aluminum metal and aluminum chloride, the mole ratio of aluminum metal to aluminum chloride is from about 15:1 to about 1:3. More preferredly, the mole ratio of aluminum metal to aluminum chloride is about 4:1 to 1:2. When the ortho-alkylation catalyst is a combination of aluminum chloride and an alkali metal, the mole ratio of alkali metal to aluminum chloride is from about 3:1 to 1:2.

After the ortho-alkylation step, the reaction mixture is treated with a hydrogen halide, either as a gas, an amine salt or other suitable anhydrous salt. Suitable hydrogen halides include hydrogen chloride, hydrogen bromide and hydrogen iodide. The preferred hydrogen halide is hydrogen chloride. The hydrogen halides can be used in the form of an amine salt such as the aniline or diphenylamine salt of the halogen halide like the diphenylamine-hydrochloride salt. The hydrogen halide is used in about a 3:1 molar ratio of hydrogen halides to the aluminum complex catalyst. The hydrogen halide can be added directly to the reaction mixture following the ortho-alkylation by mixing in the salt form or by aspirating the mixture with hydrogen halide gas. Levels of hydrogen halides above 3:1 may be used without adverse effects. The temperature at which the hydrogen halide is added can range from about room temperature up to about 100° C. The treatment of the ortho-alkylated diphenylamine intermediate with hydrogen halides leads to the formation of the Friedel-Crafts aluminum catalyst used in the para-alkylation step.

Following the formation of the Friedel-Crafts aluminum catalyst, the para-alkylation of the diphenylamine is carried out. In this step, the ortho-alkylated diphenylamine intermediate is reacted with a second olefin containing from 2 to about 16 carbon atoms following a typical Friedel-Crafts reaction process. After the para-alkylation reaction has taken place, the final ortho-para-alkylated diphenylamine product is separated from the reaction mixture in any known and desired manner.

The mechanism of the ortho- and para-alkylation reactions is postulated as follows:
1. First, the diphenylamine interacts with aluminum to form the reactive aluminum complex

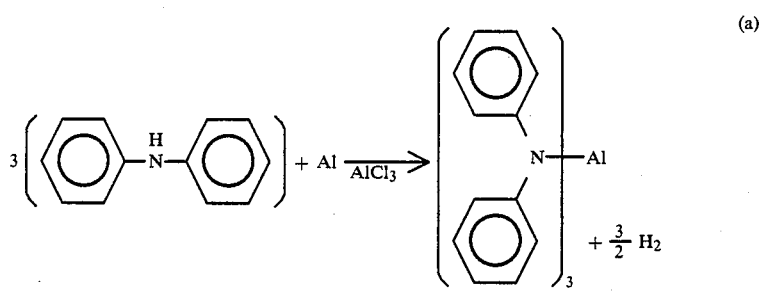

(a)

or

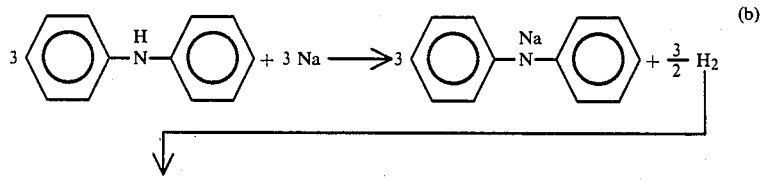

(b)

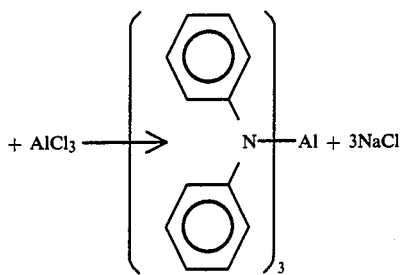

2. Then the aluminum complex reacts with the first olefin to form an ortho-alkylated intermediate product

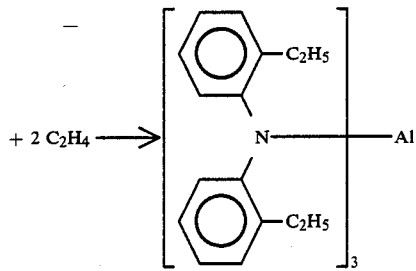

3. After the ortho-alkylation step, the hydrogen halide is added to the ortho-alkylated diphenylamine intermediate product to form the Friedel-Crafts aluminum catalyst for the para-alkylation reaction.

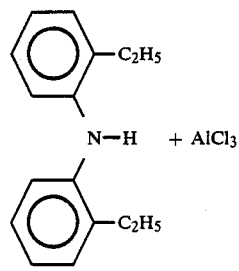

4. With the addition of the second olefin, the para-alkylation occurs through a carbonium ion mechanism following a typical Friedel-Crafts reaction process.

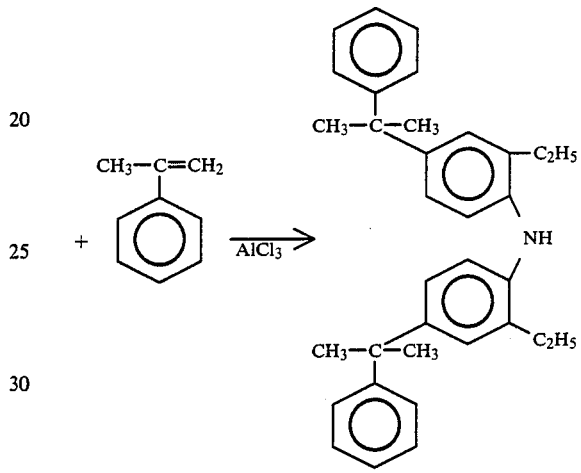

The present inventive process is carried out without isolation or solvent washing of the ortho-alkylated diphenylamine intermediate, as is disclosed in the prior art processes. The following Examples are presented to illustrate the present inventive process, but are not to be construed as limiting the invention.

EXAMPLE I

The ortho-alkylated diphenylamine intermediate was prepared as follows. 300 grams of diphenylamine were placed in a reactor equipped for agitation. 17.2 grams of $AlCl_3$ was first added for safety reasons followed by 6.0 grams of sodium metal, and the mix stirred for about 4 hours at a temperature of about 140° C. During this time the $H_2$ formed was vented. The first olefin (ethylene) was then introduced into the mixture as a gas, and the olefin and aluminum complex was heated to about 200° C. at a pressure of about 100 psig for about 6 hours. The resultant product was not isolated and recovered but can be used as is to prepare the para-alkylated product as shown in the following examples.

EXAMPLE II 200 grams of (unwashed) 2,2'-diethyldiphenylamine prepared as in Example I were charged to a dry 500 ml round-bottom flask. A catalyst of dry aniline-hydrochloride salt (17.75 g) was added with mixing. The flask was purged with dry nitrogen gas to maintain an anhydrous system. The temperature of the mixture increased from 24° C. to 34° C. in about 4 minutes indicating an exothermic reaction. The mixture was then heated to 100° C. to 140° C. and 250 ml (220 g) of α-methylstyrene was added. The reaction medium was maintained at 120° C. to 125° C. for about 12 hours. The product was recovered and analyzed by gas chromatographic and high performance liquid chromatographic methods, and shown to be 4.4% by weight 2,2'-diethyldiphenylamine; 30.0% by weight 2,2'-diethyl-4-(α,α-dimethylbenzyl)diphenylamine; and 48.8% by weight 2,2'-diethyl-4,4'-bis-(α,α-dimethylbenzyl)diphenylamine.

EXAMPLE III 206.5 grams of (unwashed) 2,2'-diethyldiphenylamine prepared as in Example I were charged to a 1000 ml round-bottom flask. Hydrogen chloride gas was dispensed into the system while stirring, and the temperature of the mixture rose to approximately 60° C. The system was then purged with dry nitrogen gas while heated to 120° C. 307.1 grams of diisobutylene ($C_8H_{16}$) was added to the flask and the mix stirred for approximately 10 hours. The product was recovered and analyzed to show 0.38% by weight 2,2'-diethyldiphenylamine; 10.12% by weight 2,2'-diethyl-4-octyldiphenylamine; and 80.7% by weight 2,2'-diethyl-4,4'-dioctyldiphenylamine.

EXAMPLE IV 300 grams of (unwashed) 2,2'-diethyldiphenylamine prepared as in Example I were treated with 6.94 grams of hydrogen chloride gas and charged into a 1.2 liter autoclave. 476 grams of a mixture of nonenes were added to the autoclave and the mix heated to 180° C. After 4 hours, 748 grams of product were obtained. The product was washed with water and unreacted nonenes were removed under vacuum. The recovered product was analyzed and shown to be 2% by weight 2,2'-diethyldiphenylamine; 33.2% by weight 2,2'-diethyl-4-nonyldiphenylamine; and 60.1% by weight 2,2'-diethyl-4,4'-dinonyldiphenylamine.

The following comparative examples were run to demonstrate some of the unique aspects of this invention.

EXAMPLE A 204.0 grams of (unwashed) 2,2'-diethyldiphenylamine prepared as in Example I were mixed with α-methylstyrene (220.3 grams) following the procedure of Example II except that no hydrogen chloride was added to the mixture. No reaction of the ortho-alkylated diphenylamine intermediate with the α-methylstyrene took place after 5 hours of heating at 90° C. to 140° C. This comparative example demonstrates that the hydrogen halide must be added to the ortho-alkylated diphenylamine intermediate product to form the Friedel-Crafts catalyst needed for the para-alkylation step.

EXAMPLE B 203.2 grams of (unwashed) 2,2'-diethyldiphenylamine prepared as in Example I were mixed with α-methylstyrene (220.6 grams) following the procedure of Example II except that no hydrogen chloride was added to the mixture. In this case, however, aluminum chloride (1.97 grams) was added to the mixture. After heating for five hours at 85° C. to 140° C., no reaction of the ortho-alkylated diphenylamine intermediate took place and no para-α-methylstyrene substituted diethyldiphenylamine was found. This example shows that simple addition of the Friedel-Crafts aluminum catalyst does not provide the para-alkylation step. One must first treat the intermediate with hydrogen halide.

EXAMPLE C 200.8 grams of 2,2'-diethyldiphenylamine prepared as in Example I was washed with water and dried. The washed mix was then added to a 1000 ml round-bottom flask, and 7.2 grams of hydrogen chloride gas was added to the flask over a 30 minute period. The temperature of the mixture rose to approximately 45° C. The mixture was heated to 105° C. to 110° C. and 305.0 grams of diisobutylene was added. After 2.5 hours, no reaction had taken place. The washing step effectively removed the aluminum complex which is soluble in water.

The above mixture was then cooled to room temperature and 7.7 grams of p-toluenesulfonic acid were added. The mixture was reheated to 100° C. for an additional 2.5 hours. After this period, no reaction had taken place. This comparative example shows that, with the removal of the aluminum complex, the addition of a traditional Friedel-Crafts catalyst (p-toluenesulfonic acid) does not provide the para-alkylation step.

EXAMPLE D 200.9 grams of (unwashed) 2,2'-diethyldiphenylamine prepared as in Example I was added to a 1000 ml round-bottom flask. The mixture was heated to 60° C. and 7.4 grams of ammonium chloride ($NH_4Cl$) was added. The mixture was gradually heated to 150° C. No evolution of ammonia gas was detected during a 1.5 hour period, indicating that the ammonium chloride, as opposed to the inventor's use of hydrogen chloride, was ineffective in forming the Friedel-Crafts aluminum catalyst.

Examples I, II, III and IV above demonstrate the present invention in that the diphenylamine was ortho-alkylated and para-alkylated without isolating the intermediate ortho-substituted product. In the comparative examples, Example A demonstrates the inactive state of the aluminum complex after undergoing the ortho-alkylation stage. Without addition of the hydrogen halides, the ortho-substituted diphenylamine intermediate complex is ineffective in promoting para-alkylation. Example B shows that the mere addition of a Friedel-Crafts aluminum catalyst to the ortho-alkylated diphenylamine intermediate is not an effective means for promoting the para-alkylation reaction. Example C shows that neither hydrogen chloride nor p-toluenesulfonic acid are effective as para-alkylation catalysts where the aluminum complex used in the ortho-alkylation has been extracted from the mixture. Example D shows that ammonium chloride, as opposed to hydrogen chloride, does not function to form the Friedel-Crafts para-alkylating catalyst.

I claim:

1. An improved, one-stage process for the ortho-, para-alkylation of diphenylamines consisting essentially of (1) forming a reactive aluminum complex by the interaction of aluminum and diphenylamine(s), (2) ortho-alkylating the diphenylamines by reacting said diphenylamine(s) with a first olefin in the presence of the aluminum complex, (3) adding hydrogen halide to the ortho-alkylated diphenylamine intermediate products to form a Friedel-Crafts aluminum catalyst, and (4) subsequently para-alkylating the ortho-alkylated diphenylamine intermediates by reacting said intermediates with a second olefin in the presence of the Friedel-Crafts aluminum catalyst, wherein the para-alkylation is carried out without prior isolation or solvent washing of said ortho-alkylated intermediates.

2. A process of claim 1 wherein the first olefin is ethylene.

3. A process of claim 1 wherein the second olefin is selected from the group consisting of styrene, α-methylstyrene, isobutylene, diisobutylene, and nonenes.

4. A process of claim 1 wherein the aluminum complex is prepared by the interaction of aluminum metal with diphenylamine in the presence of aluminum chloride.

5. A process of claim 1 wherein the aluminum complex is prepared by the interaction of diphenylamine with a combination of an alkali metal and aluminum chloride.

6. A process of claim 5 wherein the alkali metal is sodium.

7. A process of claim 1 wherein the hydrogen halide is hydrogen chloride.

8. A process of claim 1 wherein the hydrogen halide is used in the form of the salt diphenylamine hydrochloride.

* * * * *